(12) United States Patent
Krumbholz

(10) Patent No.: US 10,273,431 B2
(45) Date of Patent: Apr. 30, 2019

(54) PROCESS FOR OBTAINING FREE FATTY ACID AND/OR FATTY ACID ESTER

(71) Applicant: K.D. PHARMA BEXBACH GMBH, Bexbach (DE)

(72) Inventor: Rudolf Krumbholz, Merchweiler (DE)

(73) Assignee: K.D. PHARMA BEXBACH GMBH, Bexbach (DE)

( * ) Notice: Subject to any disclaimer, the term of this patent is extended or adjusted under 35 U.S.C. 154(b) by 0 days.

(21) Appl. No.: 15/742,399

(22) PCT Filed: Jul. 6, 2015

(86) PCT No.: PCT/DE2015/100280
§ 371 (c)(1),
(2) Date: Jan. 5, 2018

(87) PCT Pub. No.: WO2017/005235
PCT Pub. Date: Jan. 12, 2017

(65) Prior Publication Data
US 2018/0195020 A1    Jul. 12, 2018

(51) Int. Cl.
*C11B 7/00* (2006.01)
*B01D 3/14* (2006.01)
(Continued)

(52) U.S. Cl.
CPC ............... *C11B 7/00* (2013.01); *B01D 1/065* (2013.01); *B01D 3/10* (2013.01); *B01D 3/12* (2013.01);
(Continued)

(58) Field of Classification Search
CPC . C11B 3/12; C11B 7/00; C11B 7/0075; C11C 1/002; C11C 1/005; C11C 1/02;
(Continued)

(56) References Cited

U.S. PATENT DOCUMENTS

| 8,590,276 | B2 | 11/2013 | Kryger et al. | |
| 2010/0166620 | A1* | 7/2010 | Gurski | B01D 1/065 422/187 |
| 2013/0292242 | A1* | 11/2013 | Hietsch | B01D 1/065 203/87 |

FOREIGN PATENT DOCUMENTS

| WO | 2009097858 A1 | 8/2009 |
| WO | 2012048792 A1 | 4/2012 |

OTHER PUBLICATIONS

Breivik, H., Concentrates, 2007, Long-chain Omega-3 Speciality Oils, Chapter 5, The Oily Press Lipid Library, vol. 21, pp. 111-140 (Year: 2007).*

(Continued)

*Primary Examiner* — Yate' K Cutliff
(74) *Attorney, Agent, or Firm* — Lucas & Mercanti, LLP; Klaus P. Stoffel

(57) ABSTRACT

A process for obtaining free fatty acid and/or free fatty acid ester, including separating a liquid mixture containing the free fatty acid and/or the fatty acid ester by contacting a vapor of the liquid mixture in a column of a distillation apparatus with condensate formed from the vapor running downward. Heat and mass transfer takes place between the vapor and the condensate on column internals. The column has at least 10 theoretical plates and the separation is conducted with a pressure drop between the top and bottom of the column of $\Delta p$ of $\geq 3.3$ mbars. Appropriately, the liquid mixture, contains polyunsaturated fatty acid, preferably omega-6 or omega-3 fatty acid and/or alkyl monoesters and/or glycerol monoesters. In one embodiment the column has at least 30 theoretical plates and the separation is conducted with a pressure drop $\Delta p$ between 3.5 mbar and 6 mbar.

13 Claims, 1 Drawing Sheet

(51) Int. Cl.
*B01D 1/06* (2006.01)
*B01D 3/12* (2006.01)
*C07C 67/54* (2006.01)
*C11B 3/12* (2006.01)
*C11C 1/00* (2006.01)
*C11C 1/02* (2006.01)
*B01D 3/10* (2006.01)
*B01D 5/00* (2006.01)
*C07C 69/587* (2006.01)

(52) U.S. Cl.
CPC ........... *B01D 3/148* (2013.01); *B01D 5/0045* (2013.01); *C07C 67/54* (2013.01); *C11B 3/12* (2013.01); *C11C 1/002* (2013.01); *C11C 1/005* (2013.01); *C11C 1/02* (2013.01); *C07C 69/587* (2013.01); *C11B 7/0075* (2013.01)

(58) Field of Classification Search
CPC .......... B01D 1/065; B01D 3/12; B01D 3/148; B01D 5/0045
See application file for complete search history.

(56) References Cited

OTHER PUBLICATIONS

Stichlmair, J.. Distillation, 2, Equipment, 2010, UllMann's Encyclopedia of Industrial Chemistry, Sixth Edition, vol. 11, pp. 455-475 (Year: 2010).*

Porter, E.A., Distillation, 2011, Thermopedia, A-Z guide to thermodynamics, heat & mass transfer, and fluids Engineering, 13 pages (Year: 2011).*

* cited by examiner

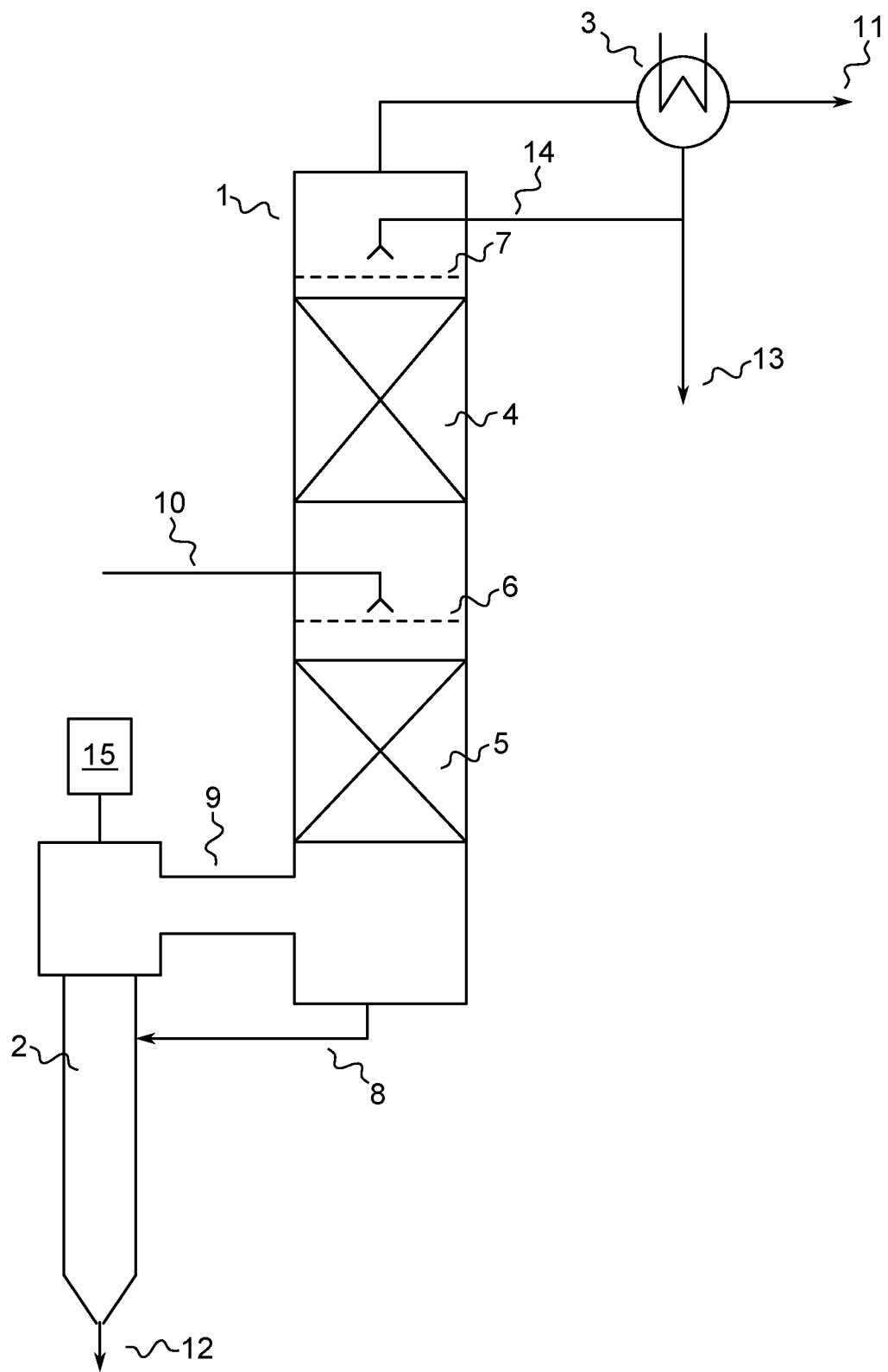

PROCESS FOR OBTAINING FREE FATTY ACID AND/OR FATTY ACID ESTER

The present application is a 371 of International application PCT/DE2015/100280, filed Jul. 6, 2015, the priority of this application is hereby claimed and this application is incorporated herein by reference.

BACKGROUND OF THE INVENTION

The invention pertains to a process for obtaining free fatty acids and/or fatty acid ester, in which, to separate a liquid mixture containing the free fatty acid and/or the fatty acid ester, a rising vapor of the liquid mixture is brought into contact in the column of a distillation apparatus with down-coming condensate formed from the vapor, wherein a mass and/or heat exchange occurs between the vapor and the condensate on internal components of the column.

To implement a process of this type, a short-path distillation, which achieves only a relatively low separation output, is usually conducted because of the considerable sensitivity of the free fatty acids or fatty acid esters to temperature. In this process, a thin film of a liquid mixture, formed on a heated evaporator surface, possibly by wiping, is partially evaporated and sent to a nearby condenser of a short-path distillation apparatus. The geometric arrangement of the evaporator surface relative to the condenser surface and the short path between them makes it possible to use working pressures in the "fine vacuum" range (from 1 mbar to $10^{-3}$ mbars) and to work with correspondingly low evaporation temperatures (compare Frank/Kutsche: Die schonende Destillation (Slow Distillation) in the "Verfahrenstechnik" ("Process Technology") series of Otto Krauskopf Verlag GmbH, Mainz, 1969).

Through use, it is also known that, to conduct the process cited above, a distillation apparatus can be used which comprises a thin-layer evaporator connected to a rectification column and a condenser. Because of the considerable temperature sensitivity of these fatty acid-containing or fatty acid ester-containing liquid mixtures, however, processing them has been considered problematic.

SUMMARY OF THE INVENTION

The invention is based on the goal of increasing the efficiency of the process described above.

According to the invention, this goal is achieved in that the column comprises at least 10 theoretical plates, and in that the separation is carried out at a pressure drop between the top and the bottom of the column of $\Delta p \geq 3.3$ mbars.

The surprising discovery was made that, when the process according to the invention is conducted, in spite of the high temperatures in the distillation apparatus required for the relatively large pressure drop, the fatty acid or fatty acid ester does not decompose or isomerize. The process offers the advantage that, because of its good separation effect, a throughput can be achieved which is greater than that of the known processes The process according to the invention is adapted in particular to the processing of liquid mixtures which contain polyunsaturated fatty acid, preferably omega-6 or omega-3 fatty acid, such as:
ALA (9Z,12Z,15Z)-octadeca-9,12,15-trienoic acid,
SDA (6Z,9Z,12Z,15Z)-octadeca-6,9,12,15-tetraenoic acid,
ETA (8Z,11Z,14Z,17Z)-eicosa-8,11,14,17-tetraenoic acid,
EPA (5Z,8Z,11Z,14Z,17Z)-eicosa-5,8,11,14,17-pentaenoic acid,
HPA (6Z,9Z,12Z,15Z,18Z)-heneicosa-6,9,12,15,18-pentaenoic acid,
DPA (7Z,10Z,13Z,16Z,19Z)-docosa-7,10,13,16,19-pentaenoic acid, and
DHA (4Z,7Z,10Z,13Z,16Z,19Z)-docosa-4,7,10,13,16,19-hexaenoic acid.

Liquid mixtures of this type are advisably produced from vegetable oil and/or fish oil and/or from microorganisms such a microalgae, yeasts, or bacteria.

In a preferred embodiment of the invention, the column comprises at least 30, and preferably at least 40, theoretical plates.

In one realization of the invention, the separation is carried out at a pressure drop $\Delta p$ in the range of 3.5 mbars $\leq \Delta p \leq 6$ mbars.

The F factor of the column is advisably no more than 2 $Pa^{1/2}$, preferably no more than 1.5 $Pa^{1/2}$, and especially preferably no more than 1.1 $Pa^{1/2}$.

In one realization of the invention, the distillation apparatus used to conduct the process according to the invention comprises a thin-layer evaporator. The previously mentioned internal components advisably comprise trays, preferably sieve trays, bell trays, or valve trays; or they can contain filler bodies and/or packings of sheet metal or wire mesh. A condenser of the distillation apparatus is advisably formed by a total condenser.

In an elaboration of the invention, a bottom product recovered at the bottom of the distillation apparatus by the separation according to the previously described process is subjected to a urea precipitation. According to this urea precipitation known from the prior art, a mixture of ethanol and urea is brought to a boil, and the bottom product is added under agitation. After the mixture has been allowed to cool, the urea cake, which has precipitated out, is separated by filtration. The ethanol present in the remaining mixture is distilled off and can, if desired, be used for additional precipitations. The mixture remaining thereafter is subjected to a short-path distillation, also known from the prior art.

In one realization of the invention, a top product recovered at the top of the distillation apparatus by the separation is processed again by the above-described process, and a second bottom product, also recovered, is mixed with a second top product recovered by means of the short-path distillation. The advantage here is that the urea precipitation, short-path distillation, and second separation of the top product makes it possible to obtain a liquid mixture highly enriched with the free fatty acid or the fatty acid ester. For example, omega-3 fatty acids highly enriched with EPA or DPA can be obtained.

The invention is explained in greater detail below on the basis of exemplary embodiments and the attached drawing.

BRIEF DESCRIPTION OF THE DRAWING

FIG. 1. schematically shows a distillation apparatus.

DETAILED DESCRIPTION OF THE INVENTION

A distillation apparatus, shown schematically in FIG. 1, was used to carry out a rectification; the apparatus comprised a thin-layer evaporator 2 equipped with a motor 15, a rectification column 1 connected to the thin-layer evaporator 2 and equipped with wire mesh packings 4, 5, and a condenser 3. The rectification column 1 had an F factor of 1 $Pa^{1/2}$ Between the bottom of the rectification column 1 and the thin-layer evaporator 2, a pipeline 8 was provided, through which the bottom product was sent to the thin-layer evaporator 2. The vapors produced in the thin-layer evaporator 2 were sent to the rectification column 1 via an exhaust vapor pipe 9, which connected the thin-layer evaporator 2 to the rectification column 1, wherein the vapor temperature above the bottom of the column was 180-210° C. The unevaporated portion was discharged from the thin-layer evaporator 2 as bottom product 12. The wire mesh packing 5 (Montz, Hilden) was arranged in the lower part of the rectification column 1 to act as a stripping section. The wire mesh packing 4 (Montz, Hilden), which acted as the rectification section I, was provided in the upper part of the column. Through a feed line 10, which opened out into the rectification column 1 between the wire mesh packings 4, 5, feed material was supplied and then uniformly distributed over the wire mesh packing 5 by a distributing device 6. At the top of the rectification column 1 was a condenser 3, by means of which the vapors emerging from the top of the rectification column 1 were condensed. A portion of the resulting condensate was returned to the column through a return line 14 and, by means of another distributing device 7, distributed uniformly over the wire mesh packing 4. Unreturned condensate was conveyed from the distillation apparatus as distillate through a discharge line 13. A vacuum line 11 led to a multi-stage vacuum pump stand, which was able to produce pressures of down to about 0.1 mbar in the top of the fractionating column 1. The distillation apparatus was able to operate with throughputs of approximately 100-600 kg/h. For the experiments described below, work was carried out at a throughput of 400 kg/h.

In the results reproduced below, "EE" stands for ethyl ester.

Example 1

A liquid mixture for processing was a feed oil containing 310 mg/g of EPA-EE and 200 mg/g of DHA-EE prior to distillation. After distillation by means of the distillation apparatus described above at a pressure difference between the bottom and the top of the distillation apparatus of $\Delta p=3.9$ mbar, bottom product amounting to 73% of the total and top product amounting to 27% of the total were obtained with approximately 50 theoretical plates at a feed rate of 400 kg/h, wherein the bottom product contained 370 mg/g of EPA-EE and 270 mg/g of DHA-EE, and the bottom product contained 150 mg/g of EPA-EE and 1.5 mg/g of DHA-EE.

Example 2

A liquid mixture for processing was a feed oil containing 360 mg/g of EPA-EE and 235 mg/g of DHA-EE prior to distillation. After distillation with the previously described distillation apparatus at a pressure difference between the bottom and the top of the distillation apparatus of $\Delta p=3.4$ mbars, bottom product in the amount of 76% of the total and top product in the amount of 24% were obtained with approximately 50 theoretical plates at a feed rate of 400 kg/hr. The bottom product contained 390 mg/g of EPA-EE and 310 mg/g of DHA-EE; the HPE top product contained 255 mg/g of EPA-EE and 1 mg/g of DHA-EE.

Example 3

A liquid mixture for processing was a feed oil containing 420 mg/g of EPA-EE and 210 mg/g of DHA-EE prior to distillation After distillation with the previously described distillation apparatus at a pressure difference between the bottom and the top of the distillation apparatus of $\Delta p=3.6$ mbars, bottom product in the amount of 74% of the total and top product in the amount of 26% were obtained with approximately 50 theoretical plates at a feed rate of 400 kg/hr. The bottom product contained 430 mg/g of EPA-EE and 280 mg/g of DHA-EE; the top product contained 400 mg/g of EPA-EE and 15 mg/g of DHA-EE.

Example 4

A liquid mixture for processing was a feed oil containing 430 mg/g of EPA-EE and 145 mg/g of DHA-EE prior to distillation. After distillation with the previously described distillation apparatus at a pressure difference between the bottom and the top of the distillation apparatus of $\Delta p=4.1$ mbars, bottom product in the amount of 70% of the total and top product in the amount of 30% were obtained with approximately 50 theoretical plates at a feed rate of 400 kg/hr. The bottom product contained 510 mg/g of EPA-EE and 205 mg/g of DHA-EE; the top product contained 230 mg/g of EPA-EE and 2 mg/g of DHA-EE.

Example 5

A liquid mixture for processing was a feed oil containing 310 mg/g of EPA-EE and 200 mg/g of DHA-EE prior to distillation. After distillation with the previously described distillation apparatus at a pressure difference between the bottom and the top of the distillation apparatus of $\Delta p=3.9$ mbars, bottom product in the amount of 73% of the total and top product in the amount of 27% were obtained with approximately 50 theoretical plates at a feed rate of 400 kg/hr, wherein the first bottom product contained 370 mg/g of EPA-EE and 270 mg/g of DHA-EE, and the first top product contained 150 mg/g of EPA-EE and 1.5 mg/g of DHA-EE.

The first bottom product was then subjected to urea precipitation. For this step, a mixture of three parts ethanol and one part urea was first brought to a boil, and then the first bottom product was added under agitation. After the mixture cooled, the urea cake which had precipitated from the mixture was separated by filtration, and the ethanol was distilled off from the remaining mixture. The mixture thus remaining was then subjected to short-path distillation at a feed rate of 200 kg/hr, an evaporator jacket temperature of 180-205° C., and a pressure of 0.01-0.1 mbar. The second top product obtained by short-path distillation contained 490 mg/g of EPA-EE and 310 mg/g of DHA-EE.

The first top product was distilled again in a distillation apparatus according to the invention. The second bottom product thus obtained contained a fatty acid ethyl ester mixture containing 610 mg/g of EPA-EE and 6 mg/g of DHA-EE.

By mixing the second bottom product and the second top product together in a ratio of 40:60, an intermediate product was then obtained in the form of a fatty acid ethyl ester mixture containing 538 mg/g EPA-EE and 188 mg/g DHA-EE. This was saponified by mixing it with ethanol (96%) and 0.617 kg of NaOH and heating it to 60° C. After an hour, the mixture was cooled to room temperature and adjusted with dilute sulfuric acid to a pH of 5. The aqueous phase and the oil phase were separated from each other, and the oil phase was washed. The oil phase was then distilled under vacuum, so that the water content of the oil phase was below 0.1%. Thus, by means of subsequent acidification, a product consisting of 538 mg/g of EPA and 188 mg/g of DHA in the form of the free fatty acid was obtained.

Example 6

A liquid mixture for processing was a feed oil containing 320 mg/g of EPA-EE and 200 mg/g of DHA-EE prior to distillation. After distillation with the previously described distillation apparatus at a pressure difference between the bottom and the top of the distillation apparatus of $\Delta p=3.5$ mbars, bottom product in the amount of 74% of the total and top product in the amount of 26% were obtained with approximately 50 theoretical plates at a feed rate of 400 kg/hr. The bottom product contained 370 mg/g of EPA-EE and 270 mg/g of DHA-EE; the HPE top product contained 190 mg/g of EPA-EE and 1 mg/g of DHA-EE.

The first bottom product was then subjected to urea precipitation as described above and then to short-path distillation. The second top product obtained by means of the short-path distillation contained 490 mg/g of EPA-EE and 310 mg/g DHA-EE.

The first top product was distilled again in a distillation apparatus according to the invention. The second bottom product thus obtained contained a fatty acid ethyl ester mixture with 630 mg/g of EPA-EE and 3 mg/g of DHA-EE.

By mixing the second bottom product and the second top product together in a ratio of 40:60, a fatty acid ethyl ester mixture with 546 mg/g of EPA-EE and 187 mg/g of DHA-EE was then obtained as the end product.

The invention claimed is:

1. A process for obtaining polyunsaturated free fatty acid and/or fatty acid ester, comprising separating a liquid mixture containing the polyunsaturated free fatty acid and/or the fatty acid ester by bringing rising vapor of the liquid mixture into contact in a column of a distillation apparatus with downcoming condensate formed from the vapor, wherein a mass and heat exchange takes place between the vapor and the condensate on internal components of the column, wherein the column comprises at least 10 theoretical plates, and the separating is carried out at a pressure drop between a top and a bottom of the column of $3.3 \leq \Delta p \leq 6$ mbars.

2. The process according to claim 1, wherein the liquid mixture contains polyunsaturated fatty acid, and/or alkyl and/or glycerol monoester.

3. The process according to claim 2, wherein the mixture contains omega-6 or omega-3 fatty acid.

4. The process according to claim 1, wherein the liquid mixture is produced from vegetable oil and/or from fish oil and/or from microorganisms.

5. The process according to claim 1, wherein the column comprises at least 30 theoretical plates.

6. The process according to claim 5, wherein the column comprises at least 40 theoretical plates.

7. The process according to claim 1, wherein the separating is carried out at a pressure drop of $\Delta p \geq 3.5$ mbars.

8. The process according to claim 1, wherein the column has an F factor of no more than 2 $Pa^{1/2}$.

9. The process according to claim 8, wherein the F factor is no more than 1.5 $Pa^{1/2}$.

10. The process according to claim 9, wherein the F factor is no more than 1.1 $Pa^{1/2}$.

11. The process according to claim 1, including evaporating the liquid mixture with a thin-layer evaporator of the distillation apparatus.

12. The process according to claim 1, further including subjecting first bottom product, obtained at a bottom of the distillation apparatus by the separating, to urea precipitation and then to short-path distillation to obtain a second top product.

13. The process according to claim 12, further including processing a first top product, obtained at a top of the distillation apparatus by the separating, again by the process and mixing a second bottom product thus obtained with the second top product obtained by the short-path distillation.

* * * * *